US00PP18973P2

(12) United States Plant Patent
Utecht

(10) Patent No.: US PP18,973 P2
(45) Date of Patent: Jun. 24, 2008

(54) ***PELARGONIUM* PLANT NAMED 'FISRELLO'**

(50) Latin Name: *Pelargonium×hortorum*
Varietal Denomination: Fisrello

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 43 days.

(21) Appl. No.: 11/506,076

(22) Filed: Aug. 17, 2006

(51) Int. Cl.
*A01H 5/00* (2006.01)

(52) U.S. Cl. ..... Plt./324
(58) Field of Classification Search ..... Plt./324, Plt./325, 328, 327
See application file for complete search history.

(56) References Cited
PUBLICATIONS
COPF Newsletter Source for information on Plant Royalities, vol. 17, No. 2; Jul. 2005, pp. 1–8.*
Floranova–Plant Breeders, Contact us, [online], [retrieved on Oct. 31, 2007. Retrieved from the internet at <http://www.floranova.co.uk/contact.php>one page.*
Upov–rom Plant Variety Database 2007/03, citation for Pelargonium 'Fisrello'and Fiv 405, 2 pages.*
* cited by examiner

*Primary Examiner*—Kent L. Bell
*Assistant Examiner*—June Hwu
(74) *Attorney, Agent, or Firm*—Jondle & Associates, P.C.

(57) ABSTRACT

A new cultivar of *pelargonium* particularly characterized by having bi-colored white and salmon-pink, semi-double, round flowers, medium-green foliage with weak zonation, a medium sized, rounded, well-branched and mounding plant habit, a high proportion of inflorescences to the foliage canopy and an early flowering response, is disclosed.

1 Drawing Sheet

Genus and species: *Pelargonium×hortorum.*
Variety denomination: 'Fisrello'.

BACKGROUND OF THE NEW PLANT

The present invention comprises a new and distinct cultivar of *pelargonium,* botanically known as *Pelargonium× hortorum,* and hereinafter referred to by the cultivar name 'Fisrello'. The new cultivar is a product of a planned breeding program which had the objective of creating a range of new medium-sized varieties having light-pink or light-salmon flowers, a good stability of flower color and medium-green foliage. 'Fisrello' was discovered as a seedling resulting from the self-pollination of the proprietary *pelargonium* plant 'I92-61-2' (unpatented), having light-pink to white, semi-double flowers.

The new cultivar was created in 1993 (self-pollination occurred in 1993 and selection of the off-spring occurred in 1994) in Hillscheid, Germany and has been asexually reproduced repeatedly by vegetative cuttings in Galdar, Gran Canaria, Spain, and Hillscheid, Germany over a twelve-year period. It has also been found to retain its distinctive characteristics through successive asexual propagations. 'Fisrello' reproduces true to type in successive generations of asexual reproduction.

Plant Breeder's Rights for this cultivar were applied for in Germany on Apr. 4, 2005 and Canada on Apr. 20, 2005.

SUMMARY OF THE INVENTION

The following are the most outstanding and distinguishing characteristics of this new cultivar when grown under normal horticultural practices in Hillscheid, Germany.

1. Semi-double, bi-colored light salmon-pink to white flowers;
2. Floriferous with medium-sized inflorescences;

3. Medium-green foliage with weak zonation;
4. A medium sized plant habit;
5. A rounded, well-branched and mounding plant habit; and
6. An early flowering response.

DESCRIPTION OF THE PHOTOGRAPH

This new *pelargonium* plant is illustrated by the accompanying photograph which shows overall plant habit including inflorescences, buds, and foliage of the plant; the colors shown are as true as can be reasonably obtained by conventional photographic procedures. The photograph is of a plant approximately 14-weeks-old, un-pinched plant grown from rooted cuttings, in 14-cm pots and grown under greenhouse and outdoor conditions which approximate those generally used in commercial practice.

DESCRIPTION OF THE NEW CULTIVAR

The following detailed description sets forth the distinctive characteristics of 'Fisrello'. The data which define these characteristics were collected from asexual reproductions carried out in Hillscheid, Germany. The plant history was taken on 11-week-old, un-pinched plants in 12-cm pots in a greenhouse during late-May. Color readings were taken under natural light in mid-May from flowers grown in the greenhouse. Color references are primarily to the R.H.S. Colour Chart of The Royal Horticultural Society of London (R.H.S.) (2001).

DETAILED BOTANICAL DESCRIPTION

Classification:
*Family.*—Geraniaceae.
*Botanical.*—*Pelargonium×hortorum.*
*Common name.*—Zonal *geranium.*

Parentage:

*Parent.*—Self-pollination of 'I92-61-2' a proprietary *pelargonium* plant having light-pink to white, semi-double flowers (unpatented).

Plant:

*Form.*—Shrub, self-branching, rounded shape.

*Branching habit.*—8 to 9 branches per plant.

*Height (measured from base of the stem to the tips of the branches, excluding the inflorescence, 11 weeks old).*—15.8 cm.

*Width (plant diameter, 11 weeks old).*—32.2 cm.

*Time to produce a flowering plant.*—Plants have an average of 0.8 opened inflorescences about 8 weeks after planting rooted cuttings in Hillscheid, Germany.

*Outdoor plant performance.*—Plants continuously flower; a count in late May of 2005 in Hillscheid, Germany produced about 4 to 5 inflorescences per plant; in late summer, plants had about 15 inflorescences at 26-weeks old.

Leaves:

*Arrangement.*—Alternate.

*Immature leaf color.*—Medium green. Upper surface: RHS 137C. Lower surface: RHS 137D.

*Mature leaf color.*—Upper surface: RHS 137C (medium-green). Lower surface: RHS 137D.

*Zonation color.*—RHS 166A (brown) with a weak to medium distinctness.

*Zonation diameter.*—Inner diameter of ring: 5.0 cm. Band or belt of zonation: 1.0 cm to 1.5 cm.

*Size.*—Length: 6.0 cm to 6.5 cm. Width: 10.2 cm.

*Shape.*—Kidney-shaped with weak lobes and a wide gap between lowest lobes.

*Apex.*—Rounded.

*Base.*—Cordate.

*Margin.*—Bi-crenate, somewhat wavy.

*Texture.*—Upper surface is smooth, dull, and velvety and the lower surface is smooth with some fine pubescence, apart from some protruding veins.

*Petioles.*—Color: RHS 143C to RHS 144B (light-green). Length: 6.0 cm to 9.0 cm. Diameter: 0.3 cm. Texture: Covered with dense pubescence.

Stems:

*Stem color.*—RHS 143C (light-green).

*Anthocyanin.*—Absent.

*Length.*—8 cm to 10 cm.

*Diameter.*—0.7 cm to 0.8 cm.

*Internode length.*—0.5 cm to 1.0 cm.

*Texture.*—Appear smooth but is covered with very short pubescence.

Inflorescence bud: (Just before petals unfold).

*Shape.*—Elliptical.

*Size.*—Length: 1.5 cm to 1.7 cm. Width: 1.0 cm to 1.2 cm.

*Color of sepals.*—RHS 143C (light-green) or RHS 144B.

*Color of petals.*—Mainly RHS 49D or RHS 55D.

Inflorescence:

*Inflorescence type.*—An umbel composed of 25 to 30 flowers.

*Umbel.*—Shape: Semi-spherical. Diameter: 9.3 cm. Height (depth): 5.8 cm.

*Lastingness of umbel on the plant.*—About 16 days.

*Peduncle.*—Color: RHS 143C (light-green). Length: 18.8 cm. Diameter: 0.4 cm to 0.5 cm. Texture: With short, dense pubescence.

*Pedicel.*—Color: RHS 143C (light-green). Length: 2.9 cm. Diameter: 0.15 cm. Texture: Covered with short glandular hair.

Corolla:

*Shape of corolla.*—Shallow cup-shaped.

*Form.*—Semi-double.

*Diameter.*—5.4 cm.

*Depth.*—1.2 cm to 1.5 cm.

*Number of petals.*—7 to 9.

*Petaloids.*—Number: 0 to 2. Shape: Narrower and shorter than the petals and occasionally curled. Color: Variable from RHS 155D (white) to RHS 55C (light-pink).

*Lastingness of individual flowers on plant.*—8 days at 18° C.

*Fragrance.*—None.

Petals:

*Shape.*—Lower petals are Obovate and upper petals are nearly spatulate.

*Apex.*—Rounded.

*Base.*—Acute.

*Margin.*—Entire or very slightly crenate at the tip.

*Texture.*—The upper surface is smooth, slightly glossy and the lower surface is smooth and glabrous.

*Upper petals.*—Length: 2.5 cm to 2.6 cm. Width: 1.8 cm to 2.0 cm. Color: Upper surface: Lower part: RHS 155D (white). Upper part: RHS 55C (light-pink) and occasionally RHS 52C or RHS 55A (deeper pink). Lower surface: From RHS 155D near the base and in the middle part to RHS 55C or RHS 55D near the margins. Markings: Tiny RHS 55B (pink) veins.

*Lower petals.*—Length: 2.2 cm to 2.3 cm. Width: 1.9 cm to 2.2 cm. Color: Upper surface: Center is RHS 155D (white) while base and margins are RHS 55C (light-pink) to RHS 52C or RHS 55A (pink). Lower surface: Somewhat variable from RHS 155D (white) to RHS 55C (light-pink). Markings: Absent.

Sepals:

*Number.*—5.

*Color.*—RHS 144C (yellow-green) for both upper and lower surfaces.

*Anthocyanin.*—Absent.

*Length.*—1.0 cm to 1.2 cm.

*Width.*—Largest upper sepal: 0.3 cm. Other sepals: 0.2 cm to 0.3 cm.

*Shape.*—Lanceolate.

*Apex.*—Acute.

*Base.*—Fused.

*Margin.*—Entire.

*Texture.*—The lower (outer) surface is with sparse, relatively long hair while the upper (inner) surface is glabrous.

Reproductive organs:

*Androecium.*—Number of anthers: 5 to 7. Filament length: 0.6 cm to 0.7 cm. Filament color: RHS 155D (white). Pollen color: RHS 28B (orange). Pollen amount: Moderate.

*Gynoecium.*—Pistil: Number: 1. Length: 0.8 cm. Stigma color: RHS 50B (light-red). Stigma shape: 5 to 6 lobed. Stigma color: Between RHS 50B and RHS 50C. Style length: 0.3 cm. Style shape: Filiform (filament-like) with the lobes of the stigma at right angles.

Fruit and seed set: No seed set observed.

Disease and insect resistance: No particular resistance or susceptibility has been observed.

COMPARISON WITH PARENTAL AND COMMERCIAL CULTIVARS

'Fisrello' differs from the parent plant 'I92-61-2' (unpatented) by having leaves with more distinct zonation, while 'I92-61-2' has no leaf zonation. In addition, 'Fisrello' has a slightly deeper green foliage color than 'I92-61-2'.

'Fisrello' differs from the commercial variety 'Fisaqua' (U.S. Plant Pat. No. 15,009) in that 'Fisrello' has bi-colored white and light salmon-pink flowers, while 'Fisaqua' has light-pink to light-rose flowers. Additionally, 'Fisrello' has shorter peduncles, smaller leaves, better branching and an earlier and more continuous flowering response than 'Fisaqua'.

'Fisrello' differs from the commercial variety 'Designer Light Pink' (U.S. Plant Pat. No. 8,552) in that 'Fisrello' has bi-colored white and light salmon-pink flowers, while 'Designer Light Pink' has pink-lavender flowers.

I claim:

1. A new and distinct cultivar of *pelargonium* plant as shown and described herein.

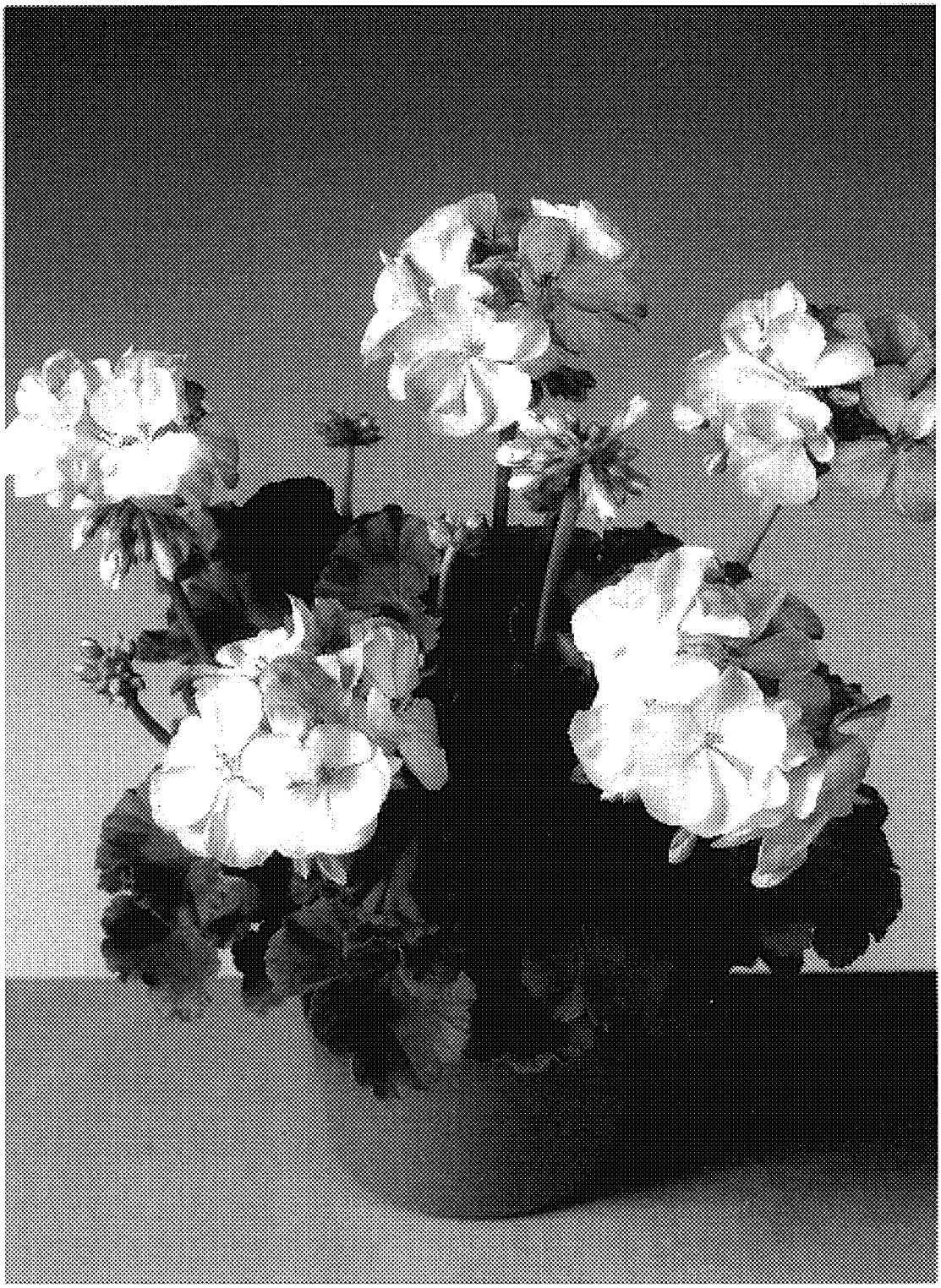

* * * * *